United States Patent [19]
Hammond et al.

[11] Patent Number: 5,917,074
[45] Date of Patent: Jun. 29, 1999

[54] PREPARATION AND APPLICATIONS OF FLUORINATED PROPARGYL PHOSPHONATE REAGENTS

[75] Inventors: Gerald B. Hammond, New Bedford; Antonio J. Zapata, Allston, both of Mass.

[73] Assignee: University of Massachusetts, Boston, Mass.

[21] Appl. No.: 08/946,146

[22] Filed: Oct. 7, 1997

[51] Int. Cl.[6] .......................................................... C07F 9/40
[52] U.S. Cl. ........................... 556/404; 525/275; 525/276; 525/331.4; 525/333.3; 525/333.4; 528/26; 528/29; 528/30; 528/32; 528/42; 556/465; 556/466
[58] Field of Search ...................................... 556/404, 465

[56] References Cited

PUBLICATIONS

Hammond et al., "Selective Fluorine Incorporation in Organic Molecules Via Vinyl– and Propargyl Fluorophosphonates", The 21st Fluorine Chemistry Debate Conference Lecture Drafts, Oct. 8–9, 1997, at Hokkaido Jichiro Meeting Hall, pp. 16–18.

Benayoud et al., "Efficient Syntheses of (α–Fluoropropargyl)phosphonate Esters", *J. Org. Chem.*, 61:5159–5164 (1996).

Blackburn et al., "A Novel Synthesis of α– and T–Fluoroalkylphosphonates", *C.S. Chem. Comm.*, 511–513 (1981).

Camps et al., "Sythesis of a Fluorinated Analog of the Sex Pheromone of the Processionary Moth", *Tetraphedron*, 42(13):3623–3629 (1986).

Cao et al., "Combinatorial Method for the Synthesis of α–Hydroxy Phosphonates on Wang Resin", *Tetrahedron Letters*, 37(34):6073–6076 (1996).

Chen et al., "Synthesis of Prostaglandin $E_2$ Methyl Ester on a Soluble–Polymer Support for the Construction of Prostanoid Libraries", *J. Am. Chem. Soc.*, 199:8724–8725 (1997).

Eddarir et al., "Synthesis of Fluorinated Enynes and Dienes Via 1–Bromo 2–Fluoro Alkenes", *Tetrahedron Letters*, 32(1):69–72 (1991).

Hagan et al., "Some influences of Fluorine in bioorganic chemistry", *Chem. Commun.*, (1997).

Lequeux et al., "Cerium–mediated Conjugate Additions of a Difluorophosphonate Carbanion to Nitroalkenes", *Letters*, 361–362 (Apr. 1995).

Lequeux et al., "Facile Synthesis of α, α–Difluror–β–ketophosphonates", *J. Chem. Soc., Chem. Commun.* 2111–2112, (1995).

Matulic–Adamic et al., "Synthesis of 5'–Deoxy–5'–difluoromethyl Phosphonate Nucleotide Analogs", *J. Org. Chem.*, 60:2563–2569 (1995).

Nieschalk et al., "Monoflurophosphonates as Phospate Mimics in Bioorganic Chemistry . . . Dehydrogenase", *J. Chem. Soc., Chem. Commun.*, 719–720 (1995).

Sanders et al., "A Regiospecific Fluroination Strategy . . . Esters", *J. Org. Chem.*, 58:5598–5599 (1993).

Sanders et al., "The crystal structure of 2–fluoro–1–(p–methoxyphenyl)–1–penten–3–yne, a fluorinated vinylacetylene . . . condensation", *J. Fluorine Chem.*, 85:2 173–175 (Oct. 1, 1997).

Yokomatsu et al., "Synthesis of (α, α–Difluoroallyl)phosphonates from Alkenyl Halides or Acetylenes", *J. Org. Chem.*, 61:7207–7211 (1996).

*Primary Examiner*—Michael G. Ambrose
*Attorney, Agent, or Firm*—Fish & Richardson P.C.

[57] ABSTRACT

The invention provides new fluorinated γ-tri-substsituted silylpropargyl phosphonates and methods for their use to generate a variety of diverse fluorine-containing compounds. The new fluorinated phosphonate synthons contain a novel juxtaposition of four different functional groups: fluoro, alkynyl, tri-substituted silyl, and phosphonato groups. The latter three of these groups provide convenient handles for the construction of fluorine-containing organic molecules.

29 Claims, No Drawings

PREPARATION AND APPLICATIONS OF FLUORINATED PROPARGYL PHOSPHONATE REAGENTS

BACKGROUND OF THE INVENTION

The invention relates to the preparation of and methods of using versatile fluorinated phosphonate synthons for constructing fluorine-containing organic compounds.

The use of fluorine in biologically active molecules is well known. One area of interest is the use of partially fluorinated phosphonates as phosphate mimics. The isosteric substitution of a hydrolytically labile ester oxygen of phosphate biomolecules by monofluoro- or difluoromethylene groups allows the latter to mimic the biological activity of the parent phosphates.

Recent reports of the antiviral and anticancer activities of partially fluorinated unsaturated phosphonucleosides have increased the demand for new methods for their synthesis (Harnden, M. R., et al. J. Med. Chem. 36, 1343–55, 1993; Megati, S., et al. J. Org. Chem. 57, 2320–27, 1992).

Syntheses of α,α-difluorophosphonates have been carried out in the past, mainly by utilizing the diethyl ester of difluoromethylene phosphonate. Other syntheses have made use of phosphonyl radical addition reactions and electrophilic fluorination.

SUMMARY OF THE INVENTION

The invention is based on the discovery that new fluorinated propargyl phosphonate synthons can be used to generate a variety of diverse fluorine-containing compounds. The new synthons contain a novel juxtaposition of four different functional groups: fluoro (which provides the desired fluorine), alkynyl, tri-substituted silyl, and phosphonato groups. The latter three of these groups provide convenient handles for the construction of a wide variety of fluorine-containing organic molecules. The invention provides novel fluorinated γ-alkyl- and γ-arylalkylsilylpropargyl phosphonates, methods for the preparation of these compounds, as well as methods of using such phosphonates to construct useful fluorine-containing organic molecules.

In general, the invention features fluorinated propargyl phosphonates, e.g., trisubstituted γ-alkyl- and γ-arylalkylsilylpropargyl phosphonates, having the structure

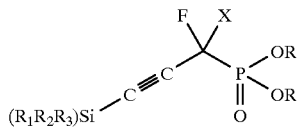

wherein $R_1$, $R_2$, and $R_3$ are, independently, alkyl or aryl; X is H or F; and each R, independently, is the same as or different than each other R, and is an alkyl or is an organic linker. For example, each of $R_1$, $R_2$, and $R_3$ can be, independently, methyl, isopropyl, phenyl, or tertiary butyl, and both Rs can be ethyl or 2,2,2-trifluoroethyl. In addition, $R_1$, $R_2$ and $R_3$ can be either all methyl, all isopropyl, or, independently, two can be methyl and the other can be isobutyl. The organic linker can be linked to a polymer.

In another aspect, the invention features a method of preparing the new fluorinated propargyl phosphonates by (a) oxidizing γ-tri-substituted silylpropargyl alcohol for a sufficient time and under conditions which allow the formation of a γ-tri-substituted silylpropargyl aldehyde; (b) reacting the γ-tri-substituted silylpropargyl aldehyde with diethyl phosphite for a time and under conditions sufficient to produce a γ-tri-substituted silylpropargyl-α-hydroxyphosphonate; and (c) fluorinating the γ-tri-substituted silylpropargyl-α-hydroxyphosphonate for a time and under conditions sufficient to produce the fluorinated propargyl phosphonate. This method can include a further step of reacting the fluorinated propargyl phosphonate with a fluorinating agent to produce α,α-difluoropropargyl phosphonate.

An alternative method can be carried out by (a) sequentially reacting a 1-tri-substituted silylpropyne with an organometallic compound and a halophosphonate for a time and under conditions sufficient to form a propargylphosphonate; and (b) reacting the propargylphosphonate with a fluorinating agent for a time and under conditions sufficient to form the fluorinated propargyl phosphonate. This method can also include the further step of reacting the α-fluoropropargyl phosphonate with a fluorinating agent to produce α,α-difluoropropargyl phosphonate.

In another aspect, the invention features a method of preparing a fluorine-containing organic compound by reacting a new fluorinated propargyl phosphonate synthon with reagents for a time and under conditions sufficient to form a fluorine-containing organic compound. For example, the fluorinated propargyl phosphonate can be reacted with an alkylating agent to form a α-alkyl-α-fluoropropargyl phosphonate, reacted with a carbonyl compound to produce an α-fluoroenyne, reacted with an activated carbonyl compound to form a fluorinated γ-ketoalkylpropargyl phosphonate, reacted with a diene to form a fluorinated Diels-Alder adduct, or reacted with an unsaturated compound to form a fluorine-containing photochemical adduct.

The invention also includes new fluoroenediynes having the structure:

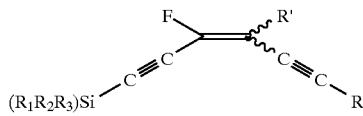

wherein $R_1$, $R_2$, and $R_3$ are, independently, alkyl or aryl; and each R and R', independently, are the same as or different than each other, and are an alkyl, an aryl, or hydrogen. The invention includes a method of preparing the new fluoroenediynes by reacting a α-fluoropropargyl phosphonate with a propargyl carbonyl compound for a time and under conditions sufficient to form a fluoroenediyne.

The invention further features a method of preparing a peptidomimic by (a) obtaining a new α-fluoroenyne; (b) carrying out a disilylation reaction to produce a desilylated α-fluroenyne; and (c) incorporating a ψ[(Z)-CF=CH] isomer of desilylated α-fluoroenyne into a peptide chain to form the peptidomimic. The invention also includes fluorine-containing organic compound prepared by the new methods, e.g., cancer-treating drugs, pharmaceuticals, anti-inflammatory drugs, nucleosides, peptidomimics, and insect sex pheromones.

A "fluorinating agent" is a chemical reagent which introduces fluorine into a chemical compound under specific conditions. A "peptide" is a chain of natural or unnatural amino acids, regardless of length or post-translational modification (e.g., glycosylation, phosphorylation), and thus includes polypeptide and proteins.

A "petidomimic" is a compound, e.g., a synthetic compound, having a three-dimensional conformation (i.e., a "peptide motif") that is substantially the same as the three-dimensional conformation of a selected peptide. The primary and secondary structure of the peptidomimic can be similar to, or different than, that of the naturally occurring peptide. The peptide motif enables the peptidomimic to modulate cellular responses with an activity that is greater than, similar to, or lesser than the activity of the peptide from which the peptidomimic was derived.

An "organic compound" is a molecule comprised of carbon, hydrogen, nitrogen, oxygen, sulphur, or phosphorus atoms, or any combination thereof. An organic compound can be a cyclic or acyclic compound formed entirely of carbon and hydrogen, or it can contain one or more heteroatoms including oxygen, nitrogen, sulfur, halogens, or phosphorus.

A "functional group," "functional moiety," "sidechain," or "substituent" is an organic group of atoms comprised of carbon, oxygen, hydrogen, halogens, nitrogen, sulfur, or phosphorus, and combinations thereof.

An "electron withdrawing group" is a moiety covalently attached to a reactant, and that is capable of decreasing the electron density in other parts of the reactant. Non-limiting examples of these are nitro, acid halide, haloalkyl, alkylcarbonyl, arylcarbonyl, aldehyde, cyano and sulfone groups.

All reagents are commercially available (e.g., Aldrich Chemical Company, Inc., Milwaukee, Wis.) and may be used after suitable purification (e.g., crystallization, distillation, sublimation, chromatographic separation).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides a number of advantages. The new fluorinated phosphonate synthons presented offer excellent building blocks for the creation of mono- or difluorine-containing phosphate mimics. They also provide convenient common starting points for the synthesis of a wide variety of complex fluorine-containing organic compounds. Thus, the invention provides simple synthetic pathways to vinyl fluorines, fluoroenynes, and fluoroenediynes. The presence of the alkyne (carbon-carbon triple bond) allows the facile introduction of both Z- and E- double bonds at the β-carbon, under different reduction conditions. Variations in the phosphonate ester groups allow control over the double bond stereochemistry at the α-carbon. The synthetic methods are simple and provide for both mono- and difluoro phosphonate synthons in good yields. Also provided is a method for polymer-based syntheses of vinylfluorine compounds which have not been reported.

Other features and advantages of the invention will be apparent from the following detailed description, and from the claims.

DETAILED DESCRIPTION OF THE INVENTION

New fluorinated propargyl phosphonate synthons include a number of convenient "handles" (functional groups) that enable the preparation of a variety of diverse fluorine-containing compounds. The new synthons can be easily prepared as described below, and can be used in simple methods to construct useful fluorine-containing organic molecules.

Fluorinated Phosphonate Synthons

The new fluorinated phosphonate synthons contain a novel juxtaposition of four different functional groups or functionalities: fluoro, alkynyl, tri-substituted silyl, and phosphonato groups. The latter three of these are convenient handles for the construction of other fluorine-containing organic molecules, including complex α-fluorophosphonates and α,α-difluorophosphonates. Fluorine itself is important for biological studies, serving as an analog of hydrogen, and —OH. Incorporation of fluorine into biological molecules has illuminated many enzymatic mechanisms. The invention provides starting materials for the synthesis of such molecules, as well as methods for converting these starting materials into useful endproducts.

The new synthons are precursors of complex fluorinated phosphonates, an important group of biological phosphate mimics, as well as analogs of phosphonate-containing molecules that have biological activity. Phosphate-containing molecules are ubiquitous in biological processes including signalling pathways, information storage and energy transfer. The isosteric substitution of a hydrolytically labile ester oxygen of phosphate biomolecules by monofluoro- or difluoromethylene groups allows the latter to mimic the biological activity of the parent phosphate. Phosphonate-containing molecules having biological activity include inhibitors of EPSP synthase, HIV protease, renin, and PTPases.

Phosphonates can exhibit important biological properties due to their similarity to phosphates. Phosphonates possess greater stability under physiological conditions than phosphates because the carbon-phosphorus bond of phosphonates is not subject to hydrolysis as is the oxygen-phosphorus bond of phosphates. In addition, alkyl phosphonate esters of nucleosides are generally more stable toward nucleases and have greater permeability into cells. Nevertheless, such analogs are still able to form stable complexes with complementary sequences.

The ability of monofluorophosphonates in compounds created from the new synthons to mimic the chemical properties of phosphates arises from the electronic similarity of the monofluoromethylene linkage to the phosphate oxygen which links phosphorus to the alkyl group. This linkage more closely resembles the phosphate linkage than either methylene ($CH_2$) or difluoromethylene ($CF_2$). For example, the $pK_a$ for the second ionization of alkylphosphates (6.4) is virtually the same as that for monofluorophosphonates (6.5), while the $pK_a$ of the methylene analog is higher (7.6) and that of the difluoromethylene analog is lower (5.4). This has been recognized as an important electronic factor in the binding of such analogs to enzymes.

Difluorophosphonates have great utility in the development of therapeutic agents. For example, a difluoromethylenephosphonate inhibitor for phosphatidylinositol-specific phospholipase C has been designed as a isosteric phosphonate substrate analog (Vinod, et al., Tet. Lett. 35, 7193–6, 1994). Fluorinated nucleosides are strong inhibitors of, for example, purine nucleoside phosphorylase (Halazy et al., J. Am. Chem. Soc. 113, 315–7, 1991).

The new synthons also provide a scaffold for the construction of organofluoro compounds. Fluoroenynes have been used to study the perception processes in insects, since they serve as analogs of sex pheromones in insects.

The fluorinated phosphonate synthons include the four above-mentioned functional groups in the following structural relationship:

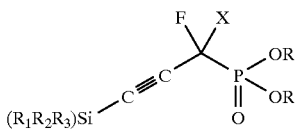

in which $R_1$, $R_2$, and $R_3$ are, independently, alkyl or aryl; X is H or F; and each R independently, is the same as, or different than, the other R and is alkyl, haloalkyl, or an organic linker. This juxtaposition allows the facile construction of other fluorine-containing organic molecules.

The presence of these functional groups acts to stabilize the α-carbanion, as well as activating the γ-carbon for attack by electrophiles. Thus, the synthon exhibits enhanced reactivities of the α-carbon, the γ-carbon, the triple bond, and the phosphonate moiety toward electrophiles, nucleophiles, transition metal-catalysed coupling reactions, and Diels-Alder cycloadditions.

Fluorine-containing compounds are of interest because of the unusual properties that compounds acquire upon introduction of fluorine substituents. The new synthons contain either one or two fluorine atoms on the α-carbon of the propargyl system. Although the Van der Waals radius of fluorine is larger than hydrogen, experimental evidence suggests that, generally, only small geometric and steric perturbations are introduced upon substitution of a single fluorine for hydrogen in methylenes. In biological systems, binding of fluorinated enzyme substrate analogs is usually not inhibited, although the electronic effect of fluorine can lead to dramatic mechanistic consequences. These can lead to mechanistic deviations and enzyme inhibition.

Replacement of both methylene hydrogens by fluorine can lead to more dramatic effects, most likely due in part to conformational differences (i.e., angle widening of adjacent atoms from the normal $sp^3$ tetrahedral angle of 109.5° to about 115–119° in —$CF_2$—). The electronic properties of fluorine also result in its being a relatively poor hydrogen bond acceptor, with a hydrogen bond strength of about half of that for oxygen.

Incorporation of a tri-substituted silyl group attached to the γ-carbon of fluoropropargyl phosphonates activates the C—Si bond towards electrophilic attack and stabilizes the α-carbanion. The presence of this group greatly increases the versatility of the synthon with respect to substituents at the γ-carbon and reactions at the α-carbon. Previous methods involving acetylenic deprotonation and alkylation of propargyl alcohols required a completely new synthesis each time a new γ-carbon substituent was desired. With the new synthons, a variety of substituents can be directly introduced at the γ-carbon without remaking the synthon. These substituents are introduced via such reactions as electrophilic additions and transition metal couplings.

The trialkylsilyl, diarylalkylsilyl, aryldialkylsilyl or triarylsilyl group also plays a role in stabilizing the carbanion at the α-carbon through hypercovalency on the silicon via a cumulene-type resonance with the α-carbanion. This effect can counteract a possible negative resonance contribution on that carbanion by the fluorine.

The alkyl groups attached to silicon can be chosen from short chain (i.e., 1 to 5 carbons) alkyl groups, such as methyl, ethyl, propyl, isopropyl, butyl, isobutyl, t-butyl, and the like. The groups may be all the same, some the same, or all different. Further examples of tri-substituted silyl substituents useful in the present invention are trimethylsilyl (TMS), triusopropylsilyl (TIPS), diphenylmethylsilyl (DPMS), and t-butyldimethylsilyl (TBDMS) substituents.

The nature of the phosphonate ester substituents can influence the stereoselectivity of the Horner-Wadsworth-Emmons (HWE) reactions (discussed below). Electron withdrawing substituents reinforce the electron-withdrawing character of the phosphonate. Suitable substituents are alkoxy groups substituted with electron-withdrawing groups such as halogens, e.g., bis(2,2,2-trifluoroethoxy).

The phosphonate ester groups can alternatively be attached via a linker group to a polymer. Reactions carried out in this way enable the solid state syntheses of many of the fluorinated compounds discussed herein. Solid state syntheses are rapidly carried out and provide pure compounds. Such methods can be used to develop combinatorial libraries of structurally related compounds, e.g., combinatorial libraries of fluorine-containing compounds. These libraries could be used, for example, in the discovery of drugs for use in the treatment of cancer, immune disorders, and inflammation, as well as in agricultural biology applications, in bioseparations, and in the development of other types of pharmaceuticals.

For reactions carried out with at least one of the reagents immobilized on either a solid support or a soluble polymer, the polymer will generally include a cleavable or noncleavable linker which connects the reagent to the solid support or soluble polymer. Suitable linkers include organic linkers e.g., alkyl or aryl chains substituted with ester, amide, ether, thioester, thioether linkages, or any other linker that can be easily cleaved if so desired. Alternatively, the linker can be noncleavable, so as to enable the synthesis of fluorine-containing organic compounds bound to the solid support or soluble polymer.

The polymer can be either a solid state resin such as a Wang resin, or a soluble polymer such as non-cross-linked chloromethylated polystyrene (NCPS). This polymer shows excellent properties, such as solubility in tetrahydrofuran (THF), dichloromethane, chloroform, and ethyl acetate, even at low temperatures (−78° C.). NCPS is insoluble in water and methanol. These features allow traditional organic chemistry techniques such as solvent extraction, and methanol precipitation. Suitable polymers include hydroxyl-containing polymers such as Wang resin, or poly(ethylene glycol) PEG. Other examples of suitable polymers are non-cross-linked polystyrene type polymers, such as non-cross-linked chloromethylated polystryene (NCPS).

The presence of a carbon-carbon triple bond (i.e., the propargyl group) allows a variety of reactions to yield, for example, cis and trans double bonds, Diels-Alder-type electrocyclic products, and photocycloaddition products. This group also provides additional stabilization of the α-carbocation through electronic resonance.

Carbon-carbon triple bonds can be reduced to give cis-double bonds by hydrogenation with diisobutylaluminum hydride (DIBALH), hydrolysis of boranes, or a variety of catalysts including activated zinc, palladium, and other palladium based catalysts such as Pd—$CaCO_3$—PbO (Lindlar's catalyst). These reactions yield cis-alkenes. Hydrazine, Li- or Na-liquid $NH_3$, $LiAlH_4$, and chromium (II) salts such as chromous sulfate pentahydrate give trans-alkenes upon reaction with alkynes.

Methods of Preparing the New Synthons

The new synthons are γ-tri-substituted silyl-α-fluoro- or α,α-difluoropropargyl phosphonates, and are synthesized by starting with propargyl alcohol. A solution of propargyl alcohol is treated with 2 equivalents of an alkylmagnesium halide (or other Grignard reagent). Tri-substituted silicon chloride is added, yielding γ-tri-substituted silyl propargyl alcohol. Typically, propargyl alcohol is protected as its tetrahydropyranyl ether before silylation.

The alcohol is oxidized to the aldehyde in a non-polar, non-protic solvent (e.g., dichloromethane) by Dess-Martin periodinane (aromatic iodonium triacetate salt). Alternatively, the oxidation can be carried out with oxalyl chloride according to Swern oxidation procedures (dimethylsulfoxide and triethylamine). The γ-tri-substituted silyl-α-hydroxypropargyl phosphonate is prepared by reacting the aldehyde with dialkyl phosphite and potassium fluoride dihydrate (alternatively triethylamine or alkali metal salts of bis(trimethylsilyl)amide) overnight for a time long enough to achieve complete phosphorylation. Generally, this takes from 2 to 20 hours. Another suitable time range is from 6 to 12 hours. If bis(2,2,2-trifluoroethoxy phosphite is used, a Lewis acid, such as AlCl$_3$, should be utilized to promote addition of phosphite to the carbonyl.

At this point, if a α,α-difluoropropargyl phosphonate is the desired product, the α-hydroxypropargyl phosphonate can be subjected to modified Pfitzner-Moffatt oxidation. The reaction is carried out by adding 1-(3-dimethylaminopropyl)-3-ethylcarbodiimide hydrochoride (2-10 equivalents) and dichloroacetic acid (0.5-3 equivalents) to a cold solution (0° C.) of the hydroxyphosphonate, to give the α-keto phosphonate. This step was followed by treatment with from 10 to 30 equivalents of diethylaminosulfurtrifluoride (DAST) at low temperatures (below 0° C., for example from 0° C. to -80° C.) under a dry, inert atmosphere (N$_2$ or Ar) to give the desired difluoropropargyl phosphonate.

Alternatively, treatment of the monofluorinated product with DAST or the Ishikawa reagent (PCR, Gainesville, Fla.) yields the desired γ-tri-substituted silyl-α-fluoropropargyl phosphonate (conditions as above).

The γ-tri-substituted silyl-α,α-difluoropropargyl phosphonate can also be prepared with the monofluoro phosphonate as a starting material by fluorinating the same with alkali metal salts of bis(trimethylsilyl)amide, and N-fluorobenzenesulfonimide (NFSI) or SELECTFLUOR™ (Air Products & Chemicals, Inc., Allentown, Pa.).

This reaction pathway is shown in Scheme 1.

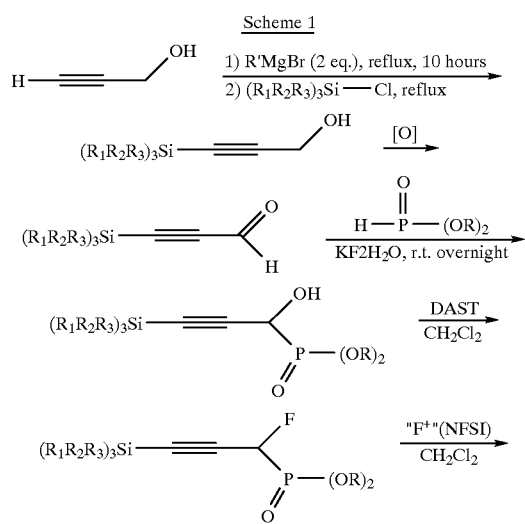

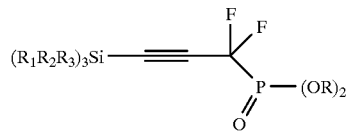

Alternatively, the synthesis can carried be out in a slightly different manner. Propargyl alcohol is reacted with para-toluenesulfonic acid (PPTS) and a protecting group such as a trialkylsilyl or diphenylalkylsilyl group or dihydropyran (DHP) in a polar, aprotic solvent. This is followed by treatment with n-butyllithium and tri-substituted silyl chloride at low temperature (0° C. or below, such as between 0° C. and -20° C.). This is followed by treatment with PPTS in a polar, protic solvent such as an alcohol. Ethanol is suitable for this purpose. This is followed by oxidation with pyridinium chlorochromate (PCC) in a nonpolar aprotic solvent at room temperature. Methylene chloride is suitable for this purpose. Reaction with diethylphosphite and a basic reagent such as potassium difluoride hydrate (KF$_2$H$_2$O), triethylamine (TEA), or sodium bis(trimethylsilyl)amide yields γ-tri-substituted silyl-α-hydroxypropargyl phosphonate. This product can be subjected to modified Pfitzner-Moffatt oxidation. The reaction is carried out by adding 1-(3-dimethylaminopropyl)-3-ethylcarbodiimide hydrochoride (2-10 equivalents) and dichloroacetic acid (0.5-3 equivalents) to a cold solution (0° C.) of the hydroxyphosphonate, to give the α-keto phosphonate. This is followed by treatment with DAST in an aprotic, nonpolar solvent such as methylene chloride (under an inert atmosphere (N$_2$ or Ar) and anhydrous conditions, at 0° C. or below, for example 0° C. to -80° C.) to give γ-triakylsilyl-α,α-difluoropropargyl phosphonate.

As described above, the α-hydroxypropargyl phosphonate itself can be reacted with DAST in in an aprotic, nonpolar solvent such as methylene chloride at low temperatures under a dry, inert atmosphere to give γ-tri-substituted silyl-α-fluoropropargyl phosphonate.

The γ-tri-substituted silyl-α-fluoropropargyl phosphonate can also be synthesized by reacting 1-tri-substituted silyl-1-propyne with a sodium, lithium, or potassium salt of bis (trimethylsilyl)amide, lithium diusopropylamide, or n-butyl lithium in tetrahydrofuran (THF) at -20° C., followed by the addition of diethyl chlorophosphate. After workup with saturated aqueous ammonium chloride, ether extraction, drying, and chromatographic separation, the product γ-tri-substituted silylpropargyl phosphonate is isolated. The product can be subsequently added as a THF solution to a solution of sodium bis(trimethylsilyl)amide in THF at -80° C. A fluorinating agent such as SELECTFLUOR™ (Air Products & Chemicals, Inc., Allentown, Pa.) or solid N-fluorobenzenesulfonimide (NFSI) can be added, the mixture is then allowed to warm, is poured into water, and finally extracted into ether. The extracts are dried, concentrated, and purified by chromatography. The resulting product is γ-trisubstituted silyl-α-fluoropropargyl phosphonate, which is used to make the α,α-difluoro phosphonate via fluorination, as described above.

This reaction pathway is shown in Scheme 2.

Scheme 2

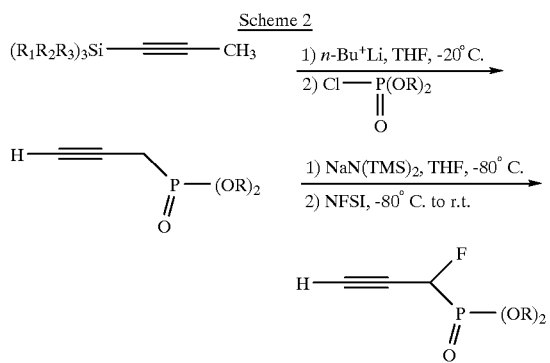

Reactions of the New Synthons

The new fluorine-containing synthons can be used to provide a plethora of fluorine-containing organic compounds through a variety of synthetic methods. These methods include reactions providing modifications at the α-carbon, the γ-carbon, the triple-bond, and the phosphonate moiety, or combinations of these modifications.

Nucleophilic Alkylations at the α-Carbon

The γ-tri-substituted silyl-α-fluoropropargyl phosphonates allow considerable stabilization of the α-carbanion due to the synergistic effect of the combined electronic characters of the fluorine, phosphonate, carbon-carbon triple bond, and tri-substituted silyl groups. This feature greatly facilitates nucleophilic addition of the α-carbanion to a variety of alkylating agents, yielding new carbon-carbon bonds.

These alkylating agents include substituted or unsubstituted compounds in the following classes: haloalkanes, alkyl tosylates, alkyl brosylates, alkyl nosylates, alkyl mesylates, and other compounds containing groups recognized in the art as being good leaving groups, as well as allylhalides, benzylhalides, and other compounds able to stabilize the positive charge developed in electrophilic addition.

The products are γ-tri-substituted silyl-α-alkyl-α-fluoropropargyl phosphonates and have the following structures:

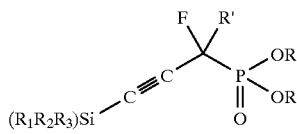

in which $R_1$, $R_2$, and $R_3$ are, independently alkyl or aryl, each R is the same or different than the other R and is alkyl, haloalkyl or an organic linker, and R' is alkyl, aryl or alkylaryl.

These reactions are generally carried out by reacting the γ-tri-substituted silyl-α-fluoropropargyl phosphonate with an alkylating reagent in the presence of a base, in a solvent, at low temperature. Suitable bases include sodium ethoxide, potassium t-butoxide, and sodamide. Suitable solvents include polar, aprotic solvents such as dimethylformamide (DMF), dimethylsulfoxide (DMSO), dioxane or tetrahydrofuran (THF). The reaction is generally carried out at low temperatures, such as below 0° C. The reactions can also be carried out at lower temperatures such as −20° C. to −100° C.

Electrophilic Substitution at the γ-Carbon

The γ-carbon of the new synthons is vulnerable to attack by electrophiles. Typically useful electrophiles are activated carbonyl-containing organic compounds, including substituted and unsubstituted organic aldehydes, such as benzaldehyde, pentanal, 2-buteneal, and 2-octynal, substituted and unsubstituted carboxylic acids and acid anhydrides, as well as acyl halides, such as benzoyl chloride. The product is a conjugated ynone.

The products are fluorinated γ-ketoalkylpropargyl phosphonates having the following structure:

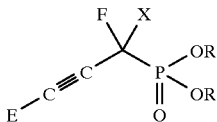

in which E is ketoalkyl, ketoaryl or ketoalkylaryl, X is F or H, and each R is the same as, or different than, the other R and is alkyl, haloalkyl or is linked to a tether.

This reaction is facilitated by the presence of Lewis acid catalysts, such as metal halides. Useful examples are aluminum trihalides, e.g., $AlCl_3$. This reaction can be carried out at low temperatures, such as below 0° C. Other suitable temperature ranges include from 0° C. to −100° C., or from −20° C. to −80° C.

Reactions with Carbonyls

Homer-Wadsworth-Emmons (HWE) reactions of the γ-tri-substituted silyl-α-fluoropropargyl phosphonates with substituted or unsubstituted aliphatic, aromatic, or propargyl aldehydes result in the formation of conjugated fluoroenynes and fluoroenediynes, respectively, as does the reaction with substituted or unsubstituted aliphatic, aromatic, or propargyl ketones. Typically useful aliphatic aldehydes are pentanal and 3-chloropent-2-enal. Typically useful aromatic aldehydes are benzaldehyde and p-hydroxybenzaldehyde. Substitutents can be any containing alkyl, carboxylic acid, amine, amide, alcohol, cyano, nitro, heterocyclic or amino acid groups. Typically useful aliphatic ketones include cyclopenanone and methylvinyl ketone. Typically useful aromatic ketones include benzophenone and p-hydroxyacetophenone. Substitutents can be any containing alkyl, carboxylic acid, amine, amide, alcohol, cyano, nitro, heterocyclic or amino acid groups. The fluoroenyne products are extremely useful as peptide isosters.

Typically useful propargyl aldehydes and ketones include 2-octynal and non-3-yn-2-one. The fluoroenediyne products can serve as models for the active enediyne moiety recently found in naturally occurring antibiotics and anticancer agents including esperomicin $a_1$ and calicheamicin $γ_1$. The Bergman rearrangement of enediynes leads to p-diradical benzene structures. The use of fluoroenediynes is expected to illuminate the reaction mechanism by altering the rate of the rearrangement.

The γ-tri-substituted silyl-α-fluroenyne products have the following general structure:

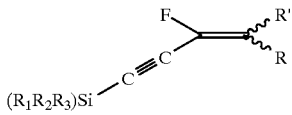

in which $R_1$, $R_2$, and $R_3$ are, independently alkyl or aryl, and R and R' are alkyl or hydrogen.

The γ-tri-substituted silyl-a-fluoroenediyne products have the following general structure:

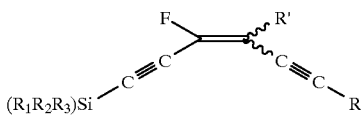

in which $R_1$, $R_2$, and $R_3$ are, independently alkyl or aryl, and R and R' are alkyl or hydrogen.

The reaction is generally carried out in the presence of a base, such as sodium ethoxide, alkali metal salts of bis(trimethylsilyl)amide or sodamide, in a polar, non-protic solvent such as THF, DMSO or HMPA. The reactions are carried out at low temperatures, for example below 0° C. Suitable temperature ranges are from 0° C. to −100° C., or from −20° C. to −80° C. The reagents are mixed and allowed to warm up to room temperature overnight.

In the HWE reaction path, the trans-fluoroalkene moiety, ψ[(Z)-CF═CH], is a potentially useful peptidomimic. That is, it is viewed as a functional substitute for the amide bond in peptides, based on its planar geometry, molecular weight, and direction of polarization. The synthons developed herein play a critical role in the synthesis of peptide mimics because they are equipped with the necessary elements for interconversion into ψ[(Z)-CF═CH] via the HWE reaction, assuming the stereoselectivity of the resulting enzyme can be controlled.

As mentioned above, the stereoselectivity of the HWE reaction can be influenced by the nature of the phosphonate ester substituents. Increasing the electron-withdrawing power of the phosphonate ester substituents results in increasing the proportion of (Z) alkenes. Substituents which can accomplish this are substituted alkoxy groups, and good examples are the halogenated alkoxy substituents. For example, this can be accomplished with bis(2,2,2-trifluoroethoxy) groups.

Solid Phase Condensations with HWE

The HWE reaction can also be used in the solid phase to obtain conjugated fluoroenynes. Fluoroenynes have been used to investigate the perception processes of insects, as analogs of sex pheromones in insects. The solid phase syntheses of organic compounds is important in the field of combinatorial chemistry. The HWE reactions outlined above can be adapted to the solid phase synthesis of fluoroenynes. This provides the first example of the solid phase synthesis of vinylfluoro compounds.

The preparation is carried out by reacting a hydroxy-containing resin (e.g., a Wang resin) with a halophosphorin, such as 2-chloro-4H-1,3,2 -benzodioxaphosphorin-4-one, in $CH_2Cl_2$/pyridine, followed by cleavage with $NaHCO_3$-TEA to produce a triethylamine salt of a polymer-linked phosphite. Reaction of this salt with pivaloyl chloride, and subsequent reaction with a nucleophile (e.g., an alcohol) yields a polymer-linked phosphonate ester which is used as a common precursor to synthesize fluorine-containing organic compounds in the solid state.

Reaction of the polymer-linked phosphonate ester with a unsubstituted or γ-substituted propargyl aldehyde yields a polymer-linked α-hydroxypropargyl phosphonate. Treatment of this species with a fluorinating agent, e.g., diethylaminosulfurtrifluoride (DAST) or SELECTFLUOR™ (Air Products & Chemicals, Inc. Allentown, Pa.) at low temperatures (below 0° C., for example 0° C. to −80° C.) in a dry, inert atmosphere ($N_2$ or Ar), yields the polymer-linked α-fluoropropargyl phosphonate. HWE reaction of this species with a carbonyl compound, such as a ketone or aldehyde, under basic conditions cleaves the product fluoroenyne from the polymer. The E:Z stereochemistry of this reaction is roughly 1:1.

Reactions with Transition Metal Complexes

The silylalkyne moiety can be targeted for use as a platform for coupling reactions using Pd, Zr (e.g., $Cp_2ZrHCl$; Schwartz's reagent) and Ru catalysts. Palladium reagents are exemplified by bis($PPh_3$)$PdCl_2$. Another useful reagent is ruthenium tetrakis($PPh_3$)$_4$. The reactions are generally carried out in polar, aprotic solvents like THF, DMSO, or hexamethylphosphoramide (HMPA) at low temperatures such as 0° C. to −100° C. or from −20° C. to −80° C.

The products of metal coupling reactions have the following general structure:

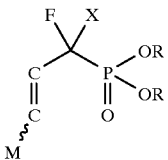

in which M is a metal complex such as bis(cyclopentadienyl)zirconium hydrochloride, tetrakis(triphenylphosphine) ruthenium, bis(triphenyl-phosphine) palladium dichloride, or tetrakis(triphenylphosphine) palladium, X is F or H, and each R is the same as, or different than, the other R and is alkyl, haloalkyl, or an organic linker.

The reactions are generally carried out by first desilylating the synthon. This is accomplished by reaction with a halide, such as fluoride, followed by hydrometallation with one of the metal complexes named above, to give the fluorinated γ-propenyl phosphonate metallocomplex. This species serves as a useful gateway for a wide variety of transformations such as reactions with Michael acceptors in the presence of Ni(AcAc)$_2$, iodination to produce vinyliodide phosphonates, and copper coupling reactions followed by reaction with epoxides or Michael acceptors to produce a variety of fluorophosphonate hydroxides and ketones, respectively. All of the above transformations can be carried out with either the mono- or difluorophosphonates described above.

Cyclizations with Alkenes (Diels-Alder and Photocycloadditions)

The triple bond is a convenient framework for cyclization reactions. The Diels-Alder reaction can be carried out with mono- or difluorinated propargyl phosphonates using cyclic and acyclic dienes with and without inverse electron demand.

Reaction of fluorinated γ-tri-substituted silylpropargyl phosphonates with cyclic dienes such as cyclopentadiene, and cyclopentadienone result in bicyclic fluorophosphonates. The subsequent decarbonylation of the cyclopentadienone adduct provides a facile entry into the realm of substituted benzylic fluoro- and difluorophosphonates. These classes of compounds represent an important mimic of O-phosphotyrosyl residues, key factors in signal transduction pathways. Reaction with acyclic dienes containing electron-withdrawing groups such as esters is also contemplated. For example, reaction of fluoropropargyl phosphonates with ethyl pentadienoate is quite suitable. These reactions are generally carried out at elevated temperatures such as 30° C. to 100° C., or for example, 50° C. to 80° C. Lewis acid catalysts such as $AlCl_3$ can be used. Solvents useful for these reactions include polar, aprotic solvents such as DMF, DMSO, and $CH_3CN$, as well as nonpolar, aprotic solvents such as methylene chloride.

Photocycloadditions with the fluorinated propargyl compounds are also possible. Such reactions include [2+2] photocycloadditions with alkenes to yield substituted cyclobutenes. These reactions can be carried out through either direct or sensitized excitation of either the alkynyl or alkenyl moiety. Generally, energy sufficient to excite the π,π* transition is required. This typically requires the equivalent of light energy in the 150 nm to 400 nm region. These reactions can be carried out in polar, protic solvents such as alcohols, polar aprotic solvents such as acetonitrile, apolar aprotic solvents such as methylene chloride.

Applications for the Products

Peptide Isosters

The terminal conjugated fluoroenynes produced by HWE reactions can be used to synthesize peptide analogs in which the amide linkage is replaced by a trans alkene (ψ[E-CH=CH]) to produce peptidomimics. The new peptidomimics typically have a backbone that is partially or completely non-peptide, but with side groups identical to the side groups of the amino acid residues that occur in the peptide on which the peptidomimic is based. This isosteric replacement can be used, for example, to prepare renin inhibitors.

On the basis of its planar geometry, molecular weight, and direction of polarization, the trans-fluoroalkene moiety has been regarded as a potentially useful peptidomimic. The new synthons described herein can be pivotal intermediates in peptidomimic synthesis, because they are equipped with the necessary elements for interconversion into ψ[Z-CH=CH] via HWE reactions, assuming the stereochemistry of the resulting enzyme can be controlled. This can be accomplished through control of the nature of the phosphonate ester substituents.

Use of the fluoroenynes as peptidomimetics can be accomplished by reacting the ψ[(Z)-CF=CH] isomer of a γ-tri-substituted silyl-α-fluoropropargyl phosphonate with a substituted amino aldehyde to give a substituted amino γ-tri-substituted silyl fluoroenyne with ψ[(Z)-CF=CH] stereochemistry. Removal of the tri-substituted silylpropargyl group with dicyclohexylborane hydride and hydrogen peroxide yields the desired substituted fluoroene amino acid. The fluoroene unit is located in the backbone of the amino acid. Subsequent incorporation of the fluoroene amino acid in a peptide allows the use of the compound as a peptidomimic.

Biological Phosphate Mimics

The new fluorinated propargyl phosphonates and products of reactions thereof are useful as biological phosphate mimics. Fluorinated propargyl phosphonates can be transformed into fluorine-containing phosphonic analogs of nucleotides, and fluorine-containing analogs of binding partners of phosphorylases and phosphokinases. For example, the disodium salt of 2-hydroxy phosphonyl difluoromethyl propenoic acid, an isopolar and isosteric analog of phosphenolpyruvate (PEP), can be readily prepared using the new synthons. Non-fluorinated PEP is a ubiquitous compound in biological systems, and plays an important role in glycolysis. Fluorinated PEP analogs do not have transferrable phosphates and illuminate glycolysis mechanisms through inhibition of the enzymes responsible for phosphate transfer.

In addition, purines linked to phosphates by 1,1-difluoro-2-butenyl chains can be prepared by γ-carbon desilylation/alkylation and triple-bond reduction procedures.

EXAMPLES

The invention will be further described in the following examples, which do not limit the scope of the invention described in the claims. The examples illustrate the syntheses and methods of using new fluorinated propargyl phosphonates. Also presented are typical reactions of the new phosphonates with representative classes of reagents to produce fluorine-containing organic molecules.

Example 1

Synthesis A of γ-(TIPS)-propargyl-α-fluorophosphonate

A solution of triIsopropylsilyl (TIPS)-propargyl alcohol (10.323 g, 48.6 mmol) in dichloromethane (50 mL) was added dropwise to a solution of Dess-Martin periodinane (22.63 g, 53.35 mmol) in dichloromethane (200 mL). A mildly exothermic reaction ensued and the mixture was stirred at room temperature for 30 minutes. The reaction mixture was quenched by pouring it into a mixture of aqueous NaOH (500 mL, 1 M) and ether (900 mL). The organic phase was dried (MgSO$_4$) and concentrated in vacuo. Distillation of the crude product afforded TIPS-propargyl aldehyde. The boiling point was 70–73° C. at 0.45 torr (9.8235 g, 96%). The proton nuclear magnetic resonance spectra ($^1$H NMR) were recorded in deuterochloroform (CDCl$_3$) and gave the following signals: δ 1.10 (m, 21H), 9.21 (s, 1H); $^{13}$C (CDCl$_3$) 11.2, 18.6, 101.0, 104.7, 176.8; IR (film, NaCl) v 2950, 2870, 2150, 1670, 1465, 1000, and 890 cm$^{-1}$. Analysis calculated for C$_{12}$H$_{22}$OSi: C: 68.51, H: 10.54. Found: C: 68.26, H: 10.45.

A mixture of TIPS-propargyl aldehyde (9.8169 g, 46,66 mmol), diethyl phosphite (6.2 mL, 48.13 mmol) and potassium fluoride dihydrate (11.0 g, 116.8 mmol) was stirred overnight. The reaction was taken up in ether (200 mL) and washed with water (3×50 mL). The ethereal extract was dried (MgSO$_4$) and concentrated in vacuo to afford a thick oil which changed to a waxy solid upon storage at low temperature (15.6105 g, 96%). This material (TIPS-propargyl-α-hydroxyphosphonate) was judged homogeneous by analytical TLC (50% ethyl acetate/hexanes): $^1$H NMR (CDCl$_3$) δ 1.09 (s, 21H), 1.35 (m, 6H), 4.23 (m, 4H), 4.71 (d, J=15.9 Hz, 1H); $^{31}$P NMR δ 17.9. Analysis calculated for C$_{16}$H$_{33}$O$_4$PSi: C: 55.14, H: 9.54. Found: C: 54.87, H: 9.65.

A solution of TIPS-propargyl-α-hydroxyphosphonate (3.1438 g, 9.02 mmol) in dichloromethane (50 mL) was added dropwise via cannula to a solution of diethylaminosulfurtrifluoride (DAST) (6.6 mL, 48.5 mL) in dichloromethane (100 mL) at −80° C. and the resulting reaction mixture was allowed to reach room temperature slowly overnight. The reaction was quenched carefully with saturated aqueous sodium bicarbonate (100 mL), the organic layer was separated and the aqueous layer was extracted with dichloromethane (2×50 mL). The combined organic extracts were dried (MgSO$_4$) and concentrated in vacuo to give a dark red oil. Purification of the crude product by flash chromatography (10–30% ethyl acetate/hexanes+4% triethylamine) afforded 1.3027 g (41%) of TIPS-propargyl-α-fluorophosphonate: $^1$H NMR (CDCl$_3$) δ 1.09 (s, 21H), 1.37 (t, J=7.1 Hz, 6H), 4.28 (m, 4H), 5.35 (dd, J=47.0, 12.5 Hz, 1H); $^{19}$F NMR δ −196 (d, J=79 Hz); $^{31}$P NMR δ 11.4 (d, J=79 Hz); Infrared spectra (IR) were recorded with the sample as a film, on NaCl plates, and gave the following results: v 2950, 2870, 2180, 1460, 1275, 1060, 1020 and 885 cm$^{-1}$. Analysis calculated for C$_{16}$H$_{32}$FO$_3$PSi: C: 54.83, H: 9.20. Found: C: 54.77, H: 9.23.

Example 2

Synthesis B of γ-(TIPS)-propargyl-α-fluorophosphonates

To a cold solution (−20° C.) of 1-triisopropylsilyl-1-propyne (0.8878 g, 98%, 4.43 mmol) in tetrahydrofuran (15 mL) was added n-butyllithum (2.9 mL of a 1.53 M solution in hexanes, 4.44 mmol). After 15 minutes, the resulting solution was transferred via cannula to a solution of diethylchlorophosphonate (1.0 mL, 97%, 6.71 mmol) in THF (5 mL) at −80° C. After the addition was completed, the reaction mixture was allowed to warm up to room temperature overnight. The reaction was poured into saturated aqueous ammonium chloride (50 mL) and extracted with ether (3×30 mL). The combined organic extracts were dried (MgSO$_4$) and concentrated. Flash chromatography (30% ethyl acetate in hexanes) of the residue afforded the desired phosphonate (0.200 g, 14%). $^1$H NMR (300 MHz, CDCl$_3$) δ 1.07 (s, 21H), 1.35 (t, J=7.3 Hz, 6H), 2.85 (d, J=22.2 Hz), 4.19 (m, 4H); $^{31}$P NMR δ 21.9 (s).

To a solution of sodium bis(trimethylsilyl)amide (0.70 mL of a 1 M solution in THF) in THF (1.3 mL) at −80° C. was added a solution of TIPS-propargylphosphonate (0.1966 g, 0.59 mmol) in THF (1 mL). After 1 hour, solid N-fluorobenzenesulfonimide (NFSI, 0.280 g, 0.89 mmol) was added in one portion. The reaction mixture was allowed to warm up to room temperature, poured into water (10 mL), and extracted with ether (3×10 mL). The combined organic extracts were dried (MgSO$_4$) and concentrated in vacuo. The residue was triturated with hexanes, filtrated and concentrated. The resulting oil was purified by flash chromatography (30% ethyl acetate in hexanes) to afford the desired TIPS-propargylfluorophosphonate (0.106 g, 51%). $^1$H NMR (CDCl$_3$) δ 1.09 (s, 21H), 1.37 (t, J=7.1 Hz, 6H), 4.28 (m, 4H), 5.35 (dd, J=47.0, 12.5 Hz, 1H); $^{19}$F NMR δ −196 (d, J=79 Hz); $^{31}$P NMR δ 11.4 (d, J=79 Hz); IR (film, NaCl) v 2950, 2870, 2180, 1460, 1275, 1060, 1020, and 885 cm$^{-1}$.

Example 3

Synthesis A of γ-(TIPS)-propargyl-α,α-difluorophosphonate

A cold solution (0° C.) of (0.5 mmol) γ-(TIPS)-propargyl-α-hydroxyphosphonate in DMSO-toluene is reacted with 1-(3-dimethylaminopropyl)-3-ethylcarbodlimide hydrochloride (2.5 mmol) and dichloroacetic acid (0.75 mmol) (Pfitzner-Moffatt conditions). The reaction is stirred for five hours after which the reaction is quenched with water and extracted with chloroform (3×25 mL). The organic layers are combined, washed with saturated NaHCO$_3$ (3×20 mL), dried over MgSO$_4$, filtered, and concentrated. The resulting oil is dissolved in dry methylene chloride (10 mL) and treated with DAST (0.01 mol) at 0° C. after which the stirred mixture is allowed to warm to room temperature. After stirring at 25° C. for 12 hours, the mixture is diluted with methylene chloride and transferred dropwise into KOH solution at 0° C. The aqueous layer is separated and the organic layer washed with saturated NaHCO$_3$ (3×20 mL). Organic layers are combined, dried over MgSO$_4$, filtered, and concentrated to yield γ-(TIPS)-propargyl-α,α-difluorophosphonate.

Example 4

Synthesis B of γ-(TIPS)-propargyl-α,α-difluorophosphonate

To a solution of γ-(TIPS)-propargyl-α-fluorophosphonate (0.6 mmol in 1 mL THF), is added 1.1 molar equivalents of solid N-fluorobenzenesulfonimide (NFSI) in one portion. The reaction mixture is allowed to warm up to room temperature, poured into water (10 mL) and extracted with ether (3×10 mL). The combined organic extracts are dried (MgSO$_4$) and concentrated in vacuo. The residue is triturated with hexanes, filtrated, and concentrated. The resulting oil is purified by flash chromatography (30% ethyl acetate in hexanes) to afford the desired γ-(TIPS)- propargyl-α,α-difluorophosphonate.

Example 5

Olefination of Benzaldehyde with TIPS-propargyl fluorophosphonate

To a solution of diisopropylamine (0.130 mL, 0.93 mmol) in tetrahydrofuran (5 mL) at 0° C. was added dropwise n-butyllithium (0.60 mL of a 1.53 M solution in hexanes, 0.92 mmol). After 5 minutes, the solution was cooled to −80° C. and a solution of TIPS-propargylfluorophosphonate (0.2862 g, 0.82 mmol) in tetrahydrofuran (1 mL) was added dropwise. After the addition was completed, benzaldehyde (1.1 equivalents) was added neat and the reaction mixture was allowed to reach room temperature. The reaction mixture was poured into saturated aqueous ammonium chloride (10 mL) and extracted with ether (3×15 mL). The combined organic extracts were dried (MgSO$_4$) and concentrated in vacuo. Products were purified by flash chromatography using silica gel and hexanes containing 4% of triethylamine as eluent.

Obtained in 90% yield as a circa 1:1 mixture of isomers: $^1$H NMR (CDCl$_3$) δ 1.09–1.20 (m, 21H), 6.06 (d, J=34.9 Hz, vinylic hydrogen of Z isomer), 6.59 (d, J=17.1 Hz, vinylic hydrogen of E isomer), 7.25–7.36 (m, 3H), 7.50 (d, J=7.4 Hz, corresponding to 2H aromatic of one of the isomers), 7.70 (d, J=6.9 Hz, corresponding to 2H aromatic of one of the isomers); $^{19}$F NMR δ −102 (s) and −105 (s); IR (film, NaCl) v 3060, 3030, 2950, 2870, 2150, 1690, 1470, 1135, 925 and 890 cm$^{-1}$. Analysis calculated for C$_{19}$H$_{27}$FSi: C: 75.44, H: 9.00. Found: C: 75.52, H: 8.89.

Example 6

Olefination of 2-octynal with TIPS-propargyl fluorophosphonate

The reaction was carried out as in Example 2, using 2-octynal as the carbonyl compound. Obtained in 87% yield as a circa 1:1 mixture of isomers: $^1$H NMR (CDCl$_3$) δ 0.87–0.92 (m, 3H), 1.07–1.19 (m, 21H), 1.25–1.39 (m, 4H), 1.48–1.57 (m, 2H), 2.29–2.39 (m, 2H), 5.32 (dt, J=28.8, 2.4 Hz, 1H Z isomer), 5.67 (dt, J=8.0, 2.5 Hz, 1H E isomer); $^{19}$F NMR δ −97 (s) and −102 (s); IR (film, NaCl) v 2940, 2870, 2220, 2150, 1615, 1460, 1185, 1150 and 885 cm$^{-1}$. Analysis calculated for C$_{20}$H$_{33}$FSi: C: 74.94, H: 10.38. Found: C: 74.95, H: 10.31.

Example 7

Olefination of Cyclopentanone with TIPS-propargyl fluorophosphonate

The reaction was carried out as in Example 2, using cyclopentenone as the carbonyl compound. Obtained in 74% yield: $^1$H NMR (CDCl$_3$) δ 1.10 (apparent s, 21H), 1.68–1.73 (m, 4H), 2.38–2.45 (m, 4H); $^{19}$F NMR δ −114 (s); IR (film, NaCl) v 2960, 2865, 2145, 1675, 1460, 1245, 1155 and 885 cm$^{-1}$.

Example 8

Olefination of 2-butenal with TIPS-propargyl fluorophosphonate

The reaction was carried out as in Example 2, using 2-butenal as the carbonyl compound. Obtained in 84% yield as a circa 1:1 mixture of isomers: $^1$H NMR (CDCl$_3$) δ 1.09–1.14 (m, 21H), 1.75–1.80 (m, 3H), 5.71–5.86, 6.16–6.20 and 6.30–6.40 (three multiplets accounting for 3H); $^{19}$F NMR δ –111.9 (s) and –112.4 (s); IR (film, NaCl) v 3040, 2950, 2870, 2150, 1610, 1460, 1270, 1140, 970 and 885 cm$^{-1}$.

Example 9

Olefination of Methyl Benzyl Ketone with TIPS-propargyl fluorophosphonate

The reaction was carried out as in Example 2, using methyl benzyl ketone as the carbonyl compound. Obtained in 81% yield as a circa 1:2 mixture of E:Z isomers: $^1$H NMR (CDCl$_3$) δ 1.00 (m, corresponding to 21H of isomer Z), 1.14 (m, corresponding to 21H of isomer E), 2.11 (d, J=4.0 Hz, corresponding to 3H of isomer Z), 2.20 (d, J=3.4 Hz, corresponding to 3H of isomer E), 7.23–7.36 (m, 3H), 7.41–7.50 (m,2H); $^{19}$F NMR δ –108 (s) and –112 (s); IR (film, NaCl) v 3060, 3030, 2950, 2870, 2150, 1645, 1465, 1195, 1065 and 890 cm$^{-1}$. Analysis calculated for C$_{20}$H$_{29}$FSi: C: 75.89, H: 9.23. Found: C: 75.88, H: 9.28.

Example 10

Olefination of Pentanal with TIPS-propargyl fluorophosphonate

The reaction was carried out as in Example 2, using pentanal as the carbonyl compound. Obtained in 89% yield as a circa 1:1 mixture of E:Z isomers. However, flash chromatography afforded a few fractions containing only one of the isomers. Isomer E: $^1$H NMR (CDCl$_3$) δ 0.90 (t, J=7.1 Hz, #H), 1.10 (m, 21H), 1.29–1.42 (m, 4H), 2.12–2.19 (m, 2H), 5.61 (dt, J=14.7, 8.2 Hz, 1H); $^{19}$F NMR δ –109 (s). Isomer Z: $^1$H NMR (CDCl$_3$) δ 0.90 (t, J=7.1 Hz, #H), 1.09 (m, 21H), 1.33–1.39 (m, 4H), 2.15–2.18 (m, 2H), 5.24 (dt, J=33.5, 7.8 Hz, 1H); $^{19}$F NMR δ –112 (s). IR (film, NaCl) v 2950, 2870, 2160, 1655, 1460, 1115 and 885 cm$^{-1}$. Analysis calculated for C$_{17}$H$_{31}$FSi: C: 72.27, H: 11.06. Found: C: 72.37, H: 11.04.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fluorinated propargyl phosphonate comprising the structure:

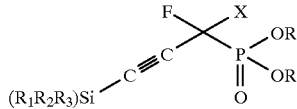

wherein R$_1$, R$_2$, and R$_3$ are, independently, alkyl or aryl, wherein not all of R$_1$, R$_2$ and R$_3$ are methyl; X is H or F; and each R, independently, is the same as or different than each other R, and is an alkyl or is an organic linker.

2. The fluorinated propargyl phosphonate of claim 1, wherein each of R$_1$, R$_2$, and R$_3$ are independently selected from the group consisting of methyl, isopropyl, phenyl and tertiary butyl, wherein not all of R$_1$, R$_2$ and R$_3$ are methyl.

3. The fluorinated propargyl phosphonate of claim 1, wherein X is F.

4. A fluorinated propargyl phosphonate of claim 1, wherein both R are ethyl.

5. The fluorinated propargyl phosphonate of claim 1, wherein both R are 2,2,2-trifluoroethyl.

6. The fluorinated propargyl phosphonate of claim 1, wherein R$_1$, R$_2$ and R$_3$ are either all isopropyl, or, independently, two are methyl and one is isobutyl, or two are methyl and one is tertiary butyl, or two are phenyl and one is methyl.

7. A method of preparing fluorinated propargyl phosphonates according to claim 1, the method comprising the steps of:
   (a) oxidizing γ-tri-substituted silylpropargyl alcohol for a sufficient time and under conditions which allow the formation of a γ-tri-substituted silylpropargyl aldehyde;
   (b) reacting the γ-tri-substituted silylpropargyl aldehyde with diethyl phosphite for a time and under conditions sufficient to produce a γ-tri-substituted silylpropargyl-α-hydroxyphosphonate; and
   (c) fluorinating the γ-tri-substituted silylpropargyl-α-hydroxyphosphonate for a time and under conditions sufficient to produce the fluorinated propargyl phosphonate.

8. A method of preparing fluorinated propargyl phosphonates of claim 1, the method comprising the steps of:
   (a) sequentially reacting a 1-tri-substituted silylpropyne with an organometallic compound and a halophosphonate for a time and under conditions sufficient to form a propargylphosphonate; and
   (b) reacting the propargylphosphonate with a fluorinating agent for a time and under conditions sufficient to form the fluorinated propargyl phosphonate.

9. A method of claim 7, further comprising the step of reacting the fluorinated propargyl phosphonate with a fluorinating agent to produce α,α-difluoropropargyl phosphonate.

10. A method of claim 8, further comprising the step of reacting the α-fluoropropargyl phosphonate with a fluorinating agent to produce α,α-difluoropropargyl phosphonate.

11. A fluorinated propargyl phosphonate of claim 1, wherein the organic linker is linked to a polymer.

12. The fluorinated propargyl phosphonate of claim 1, wherein the organic linker is linked to a solid support.

13. The fluorinated propargyl phosphonate of claim 12, wherein the organic linker is non-cleavable.

14. The fluorinated propargyl phosphonate of claim 12, wherein the organic linker is cleavable.

15. The fluorinated propargyl phosphonate of claim 14, wherein the cleavable organic linker comprises an alkyl chain containing a linkage selected from the group consisting of ester, amide, ether, thioester, and thioether linkages.

16. The fluorinated propargyl phosphonate of claim 14, wherein the cleavable organic linker comprises an aryl chain containing a linkage selected from the group consisting of ester, amide, ether, thioester, and thioether linkages.

17. The fluorinated propargyl phosphonate of claim 11, wherein the polymer is a soluble polymer.

18. The fluorinated propargyl phosphonate of claim 11, wherein the organic linker is non-cleavable.

19. The fluorinated propargyl phosphonate of claim 11, wherein the organic linker is cleavable.

20. The fluorinated propargyl phosphonate of claim 19, wherein the cleavable organic linker comprises an alkyl chain containing a linkage selected from the group consisting of ester, amide, ether, thioester, and thioether linkages.

21. The fluorinated propargyl phosphonate of claim 19, wherein the cleavable organic linker comprises an aryl chain containing a linkage selected from the group consisting of ester, amide, ether, thioester, and thioether linkages.

22. The fluorinated propargyl phosphonate of claim 17, wherein the soluble polymer is selected from the group consisting of polyethylene glycol, Wang resin, and non-cross-linked chloromethylated polystyrene.

23. The fluorinated propargyl phosphonate of claim 17, wherein the chloromethylated polystyrene is a Merrifield resin.

24. A method of preparing α-alkyl-α-fluoropropargyl phosphonate, the method comprising reacting a fluorinated propargyl phosphonate of claim 1 with an alkylating agent for a time and under conditions sufficient to form the α-alkyl-α-fluoropropargyl phosphonate.

25. A method of preparing α-fluoroenyne, the method comprising reacting a fluorinated propargyl phosphonate of claim 1 with a carbonyl compound for a time and under conditions sufficient to form the α-fluoroenyne.

26. A method of preparing a fluorinated γ-ketoalkylpropargyl phosphonate, the method comprising reacting a fluorinated propargyl phosphonate of claim 1 with an activated carbonyl compound for a time and under conditions sufficient to form the fluorinated γ-ketoalkylpropargyl phosphonate.

27. A method of preparing a fluorinated Diels-Alder adduct, the method comprising reacting a fluorinated propargyl phosphonate of claim 1 with a diene for a time and under conditions sufficient to form the fluorinated Diels-Alder adduct.

28. A method of preparing a fluorine-containing photochemical adduct, the method comprising reacting a fluorinated propargyl phosphonate of claim 1 with an unsaturated compound for a time and under conditions sufficient to form the fluorine-containing photochemical adduct.

29. A method of preparing a fluoroenediyne, the method comprising reacting a fluoropropargyl phosphonate of claim 1 with a propargyl carbonyl compound for a time and under conditions sufficient to form the fluoroenediyne.

\* \* \* \* \*